(12) United States Patent
Mallard et al.

(10) Patent No.: US 8,937,098 B2
(45) Date of Patent: Jan. 20, 2015

(54) DERMATOLOGICAL COMPOSITIONS COMPRISING AT LEAST ONE NAPHTHOIC ACID COMPOUND AND AT LEAST ONE FILM-FORMING AGENT AND TREATMENT OF KERATINIZATION DISORDERS THEREWITH

(75) Inventors: Claire Mallard, Mougins (FR); Eve Ferrara, Valbonne (FR)

(73) Assignee: Galderma Research & Development, Biot (FR)

( * ) Notice: Subject to any disclaimer, the term of this patent is extended or adjusted under 35 U.S.C. 154(b) by 510 days.

(21) Appl. No.: 12/276,584

(22) Filed: Nov. 24, 2008

(65) Prior Publication Data

US 2009/0247630 A1 Oct. 1, 2009

Related U.S. Application Data

(63) Continuation of application No. PCT/FR2007/051359, filed on May 31, 2007.

(30) Foreign Application Priority Data

May 31, 2006 (FR) ...................................... 06 51982

(51) Int. Cl.

| | | |
|---|---|---|
| A61K 31/19 | (2006.01) | |
| A61P 17/00 | (2006.01) | |
| A61K 9/00 | (2006.01) | |
| A61K 8/04 | (2006.01) | |
| A61K 8/06 | (2006.01) | |
| A61K 8/368 | (2006.01) | |
| A61K 8/73 | (2006.01) | |
| A61K 8/81 | (2006.01) | |
| A61K 31/192 | (2006.01) | |
| A61Q 5/00 | (2006.01) | |
| A61Q 17/04 | (2006.01) | |
| A61Q 19/00 | (2006.01) | |
| A61Q 19/08 | (2006.01) | |
| A61K 47/10 | (2006.01) | |
| A61K 47/18 | (2006.01) | |
| A61K 47/32 | (2006.01) | |
| A61K 47/36 | (2006.01) | |
| A61K 47/44 | (2006.01) | |

(52) U.S. Cl.
CPC ................. *A61K 9/0014* (2013.01); *A61K 8/04* (2013.01); *A61K 8/06* (2013.01); *A61K 8/368* (2013.01); *A61K 8/735* (2013.01); *A61K 8/8182* (2013.01); *A61K 31/192* (2013.01); *A61Q 5/00* (2013.01); *A61Q 17/04* (2013.01); *A61Q 19/008* (2013.01); *A61Q 19/08* (2013.01); *A61K 47/10* (2013.01); *A61K 47/18* (2013.01); *A61K 47/32* (2013.01); *A61K 47/36* (2013.01); *A61K 47/44* (2013.01)
USPC ........................................................ 514/557

(58) Field of Classification Search
None
See application file for complete search history.

(56) References Cited

U.S. PATENT DOCUMENTS

| | | | |
|---|---|---|---|
| 4,717,720 A | | 1/1988 | Shroot et al. |
| 5,529,987 A | * | 6/1996 | Gallina ........................... 514/54 |
| 5,871,754 A | | 2/1999 | Briggs et al. |
| 2003/0077301 A1 | * | 4/2003 | Maibach et al. .............. 424/400 |
| 2004/0009213 A1 | * | 1/2004 | Skold ............................ 424/449 |
| 2005/0059740 A1 | * | 3/2005 | Graeber et al. ............... 514/569 |
| 2006/0029556 A1 | | 2/2006 | Louis et al. |
| 2007/0148110 A1 | | 6/2007 | Zanutto et al. |

FOREIGN PATENT DOCUMENTS

| | | | |
|---|---|---|---|
| EP | 0 199 636 A1 | 10/1986 | |
| EP | 0781550 | * 2/1997 | .......... A61K 31/415 |
| FR | 2 837 101 A1 | 9/2003 | |
| FR | 2 871 377 A | 12/2005 | |
| WO | WO 95/04517 | 2/1995 | |
| WO | WO 2004/052353 A2 | 6/2004 | |

OTHER PUBLICATIONS

Polyvinylpyrrolidone, http://www.pharma-ingredients.basf.com/Polyvinylpyrrolidone.aspx.*
Technical Information Kollidon VA64, w ww.pharma-ingredients.basf.com/.../EMP%20050602e_Kollidon %20VA%2064_VA%2064%20Fine.pdf.*
"Hyaluronic Acid (HA) for Skin and Joints" Discount Vitamins & Herbs, May 30, 2006 pp. 1-5 XP002415428.
International Search Report PCT/FR2007/051359 dated Oct. 30, 2007.

* cited by examiner

*Primary Examiner* — Dennis Heyer
(74) *Attorney, Agent, or Firm* — Dentons US LLP

(57) ABSTRACT

Topically applicable, reduced-irritant dermatological/cosmetic compositions useful for the treatment of a variety of keratinization disorders, for example acne vulgaris, contain at least one naphthoic acid compound essentially uniformly distributed therethrough and an amount of at least one hydrophilic film-forming agent, formulated into a topically applicable, physiologically acceptable medium.

15 Claims, No Drawings

DERMATOLOGICAL COMPOSITIONS COMPRISING AT LEAST ONE NAPHTHOIC ACID COMPOUND AND AT LEAST ONE FILM-FORMING AGENT AND TREATMENT OF KERATINIZATION DISORDERS THEREWITH

CROSS REFERENCE TO PRIORITY/PCT APPLICATIONS

This application claims priority under 35 U.S.C. §119 of FR 06/51982, filed May 31, 2006, and is a continuation of PCT/FR 2007/051359, filed May 31, 2007 and designating the United States (published in the French language on Dec. 6, 2007 as WO 2007/138231 A1; the title and abstract were also published in English), each hereby expressly incorporated by reference in its entirety and each assigned to the assignee hereof.

BACKGROUND OF THE INVENTION

1. Technical Field of the Invention

The present invention relates to dermatological compositions for topical application, to processes for formulating such compositions and to their uses as cosmetic or pharmaceutical products. Said compositions are particularly useful for treating acne.

2. Description of Background and/or Related and/or Prior Art

Acne is a common multi-factor pathology that attacks skin rich in sebaceous glands (face, shoulder area, arms and intertriginal areas). It is the most commonly occurring form of dermatosis. The following five pathogenic factors play a determining role in the formation of acne:

1. genetic predisposition;
2. overproduction of sebum (seborrhoea);
3. androgens;
4. follicular keratinization disorders (comedo-genesis); and
5. bacterial colonization and inflammatory factors.

There are several forms of acne, the common factor of all being attack of the pilosebaceous follicles. Especially exemplary are acne conglobata, cheloid acne of the nape of the neck, medication-related acne, recurrent miliary acne, necrotic acne, neonatal acne, premenstrual acne, occupational acne, acne rosacea, senile acne, solar acne and simple acne.

Simple acne, also known as polymorphic juvenile acne, is the most common. It comprises four stages, but passage through all the stages is not obligatory:

stage 1 corresponds to comedonic acne characterized by a large number of open and/or closed comedones and of microcysts;

stage 2, or papulopustular acne, is of mild to moderate seriousness. It is characterized by the presence of open and/or closed comedones, microcysts, but also red papules and pustules. It mainly affects the face and leaves few scars;

stage 3, or papulocomedonic acne, is more serious and extends to the back, the chest and the shoulders. It is accompanied by a larger number of scars;

stage 4, or nodulocystic acne, is accompanied by many scars. It presents nodules and also painful voluminous crimson pustules.

The various forms of acne described above may be treated with active agents such as anti-seborrhoeic agents and anti-infectious agents, for example benzoyl peroxide (especially the product Eclaran® marketed by Pierre Fabre), with retinoids such as tretinoin (especially the product Retacnyl® marketed by Galderma) or isotretinoin (the product Roaccutane® marketed by Laboratoires Roche), or with naphthoic acid derivatives. Naphthoic acid derivatives such as, especially, 6-[3-(1-adamantyl)-4-methoxyphenyl]-2-naphthoic acid, which is commonly known as adapalene (the product Differin® marketed by Galderma), are widely described and acknowledged as active principles that are just as effective as tretinoin for the treatment of acne. Adapalene also has the advantage of causing fewer side effects, such as phenomena of irritation, dryness of the skin or intolerance, than the other active agents described above, which makes it a product of choice.

However, those skilled in the art are constantly seeking to improve the efficacy and tolerance of compositions containing this type of active agent. One of the solutions for improving the efficacy is to increase the amounts of active agents present in the composition or to increase the treatment times. Such modifications generally result in an increase in the induced irritation. This is why it is necessary to provide compositions that can further improve the tolerance of the active principles.

SUMMARY OF THE INVENTION

The present invention provides dermatological compositions that are stable and less irritant than those of the prior art. Such compositions furthermore promote the topical penetration of the active principle in dispersed form.

Thus, it has now surprisingly been discovered that ingredients that are known for providing a composition with a film-forming effect may also improve the tolerance of irritant active principles, such as anti-acne active agents, and especially naphthoic acid compounds such as adapalene.

Thus, the present invention features compositions for topical application that are particularly effective, comprising a naphthoic acid compound, without having any manifestly irritant effect that would prevent their longer- or shorter-term use by an individual.

Accordingly, this invention features compositions for topical application, comprising, in a physiologically acceptable medium, at least one naphthoic acid compound and at least one film-forming agent, said naphthoic acid compound being in dispersed form in the compositions.

According to the invention, the term "active agent in dispersed form" means an active principle in the form of solid particles, suspended in a given vehicle. Such particles are especially greater than 10 μm in size.

The present invention also features a process for preparing compositions for topical application, which comprises the step of mixing a physiologically acceptable vehicle comprising at least one naphthoic acid compound with at least one film-forming agent, said naphthoic acid compound being in a form dispersed in the compositions. The term "physiologically acceptable vehicle" means a vehicle that is compatible with the skin, mucous membranes and/or the integuments.

Finally, this invention features administration, whether regime or regimen, of the compositions as described above as medicaments for treating and/or preventing dermatological complaints associated with a keratinization disorder that has a bearing on cell differentiation and proliferation, and especially for preventing and/or treating comedonic acne, simple acne, papulocomedonic acne, nodulocystic acne, polymorphic acne, acne rosacea, acne conglobata, senile acne, or alternatively secondary acnes such as solar acne, medication-related acne or occupational acne.

When a composition comprises, in a physiologically acceptable medium, at least one naphthoic acid compound and at least one film-forming agent, the naphthoic acid compound being in a form dispersed in the said composition, same exhibits very good tolerance without modifying the amount of active agent that has penetrated into the skin.

DETAILED DESCRIPTION OF BEST MODE AND SPECIFIC/PREFERRED EMBODIMENTS OF THE INVENTION

The compositions according to the invention comprise at least one naphthoic acid compound/derivative and at least one film-forming agent.

Naphthoic acid is a compound of formula:

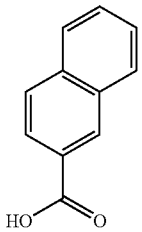

The term "naphthoic acid compound" means the compounds of formula (I):

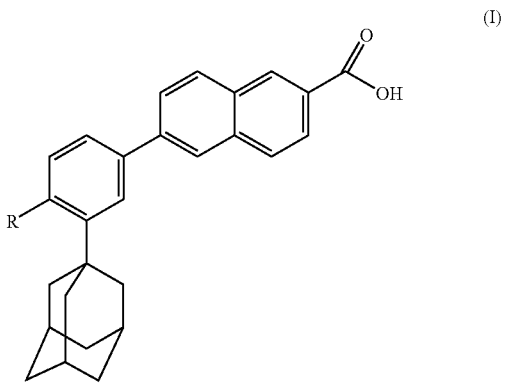

in which:

R is a hydrogen atom, a hydroxyl radical, a branched or unbranched alkyl radical having from 1 to 4 carbon atoms, an alkoxy radical having from 1 to 10 carbon atoms or a substituted or unsubstituted cycloaliphatic radical.

The term "linear or branched alkyl radical having from 1 to 4 carbon atoms" preferably means methyl, ethyl, propyl and butyl radicals.

The term "alkoxy radical having from 1 to 10 carbon atoms" preferably means methoxy, ethoxy, propoxy, butoxy, hexyloxy and decyloxy radicals.

The term "cycloaliphatic radical" preferably means monocyclic or polycyclic radicals such as the 1-methylcyclohexyl radical or the 1-adamantyl radical.

Among the naphthoic acid compounds that may be formulated into the compositions according to the invention, 6-[3-(1-adamantyl)-4-methoxyphenyl]-2-naphthoic acid (adapalene), 6-[3-(1-adamantyl)-4-hydroxyphenyl]-2-naphthoic acid, 6-[3-(1-adamantyl)-4-decyloxyphenyl]-2-naphthoic acid and 6-[3-(1-adamantyl)-4-hexyloxyphenyl]-2-naphthoic acid will advantageously be selected.

The abovementioned naphthoic acid derivatives are generally in a form dispersed in the composition according to the invention. The insoluble naphthoic acid derivatives are thus uniformly distributed in the composition according to the invention.

In the compositions according to the invention, the naphthoic acid compounds are employed at concentrations of less than or equal to 10% by weight relative to the total weight of the composition, and preferably from 0.001% to 10% by weight relative to the total weight of the composition, preferentially from 0.01% to 5%, more preferentially from 0.05% to 2% to most preferentially from 0.1% to 0.3% by weight relative to the total weight of the composition.

Throughout the present text, unless otherwise specified, it is understood that when ranges of concentrations are given, the upper and lower limits of the said range are included.

Advantageously, the naphthoic acid compound contained in the compositions according to the invention is adapalene. The adapalene concentration in the composition according to the invention is then from 0.01% to 0.5%, more preferentially from 0.1% to 0.3% to in particular at a concentration of approximately 0.1% or at a concentration of approximately 0.3%.

The compositions according to the invention also comprise at least one film-forming agent.

The term "film-forming agent" means a hydrophilic polymer with a molecular mass at least greater than 10,000, which, during application to the skin, forms a film. It has been demonstrated that, besides having gelling properties, these film-forming agents provide the composition comprised thereof better tolerance.

Exemplary such film-forming agents include polyvinylpyrrolidones, which are preferably water-soluble, such as povidone, for instance Kollidon®, and vinyl acetate derivatives, for instance copovidone, polysaccharides, polyvinyl alcohols, celluloses and derivatives, cyanoacrylic polymers or polyacrylamides, and acrylic, acrylic/methacrylic, polymethacrylate/butylacrylate and acrylic/acrylate copolymers. The water-soluble film-forming agents according to the invention may be of natural origin, such as sodium hyaluronate.

Among the polyvinylpyrrolidones and derivatives that are exemplary are poly-1-vinyl-2-pyrrolidone, also known as povidone, and the polyvinylpyrrolidone/vinyl acetate copolymer, also known as copovidone, for instance Kollidon® VA64.

Examples of polysaccharides include celluloses and derivatives, for instance carboxymethylcellulose, hydroxypropylcellulose or hydroxyethylcellulose. Among the other polysaccharides that are also exemplary are gums such as xanthan gum, guar gum, karaya gum, carrageenan gums, pectins and sodium hyaluronate.

Preferentially, the water-soluble film-forming agent according to the invention is selected from polyvinylpyrrolidones and soluble copolymers thereof, for instance copovidone, and from polysaccharides, for instance sodium hyaluronate.

In the compositions according to the invention, the film-forming agents are present at concentrations of less than or equal to 20% to preferably from 0.5% to 20% by weight, more preferentially from 1% to 10% by weight and in particular 2%, 4% or 6% by weight relative to the total weight of the composition.

The presence of at least one film-forming agent allows the tolerance to be improved and is particularly advantageous in the case of formulations comprising adapalene. The reason for this is that naphthoic acid compounds may be irritant and have a dehydrating action on the skin. It is thus advantageous to reduce the irritation induced in order to be able to increase the doses.

The compositions of the present invention may be in any galenical form normally employed for topical application, especially in the form of aqueous, aqueous-alcoholic or oily dispersions, dispersions of the lotion type, aqueous, anhydrous or lipophilic gels, emulsions of liquid or semi-liquid consistency of the milk type, obtained by dispersing a fatty phase in an aqueous phase (O/W) or vice versa (W/O), or suspensions or emulsions of soft, semi-liquid or solid consistency of the cream, cream-gel or pomade type, or alternatively microemulsions, microcapsules, microparticles or vesicular dispersions of ionic and/or nonionic type.

Preferably, the compositions according to the invention are in the form of lotions, cream-gels, gels or creams and more preferentially in the form of gels.

One skilled in the art will take care to select the excipients constituting the compositions according to the invention as a function of the desired galenical form and such that the advantageous properties thereof are respected.

The compositions according to the invention may also especially comprise one or more of the following ingredients:
a) one or more gelling agents or suspending agents,
b) one or more chelating agents,
c) one or more emollients,
d) one or more wetting agents,
e) one or more preservatives.

Exemplary gelling agents or suspending agents that may be included in the compositions according to the invention, are of the carbomers marketed under the generic name Carbopol®, the "electrolyte-insensitive" carbomers marketed under the trademark Ultrez 10® or Carbopol ETD® by BF Goodrich, polysaccharides, non-limiting examples of which include xanthan gum such as Keltrol T® marketed by Kelco, guar gum, chitosans, cellulose and derivatives thereof such as hydroxyethylcellulose, in particular the product marketed under the trademark Natrosol HHX 250® by Aqualon, and the copolymer of acrylamide and of sodium acrylamino-2-methylpropanesulfonate as a 40% dispersion in isohexadecane and polysorbate 80 marketed under the trademark Simulgel 600® by SEPPIC.

Preferred gelling agents that are exemplary are the carbomers marketed especially under the trademarks Carbopol 974P NF and Carbopol 980 NF.

Among the chelating agents, exemplary thereof are ethylenediaminetetraacetic acid (EDTA), diethylenetriaminepentaacetic acid (DTPA), ethyl-enediaminebis(O-hydroxyphenylacetic acid) (EDBHA), hydroxy-2-ethylenediaminetriacetic acid (HEDTA), ethyldiaminebis(O-hydroxy-p-methylphenyl)acetic acid (EDBHMA) and ethylenediaminebis(5-carboxy-2-hydroxy-phenyl)acetic acid (EDBCHA).

A preferred chelating agent is ethylenediaminetetraacetic acid (EDTA) marketed especially under the trademark Titriplex III®.

Among the emollients, the role of which is to hydrate the skin and facilitate the application of the formulation, compounds such as glycerol, propylene glycol, dipropylene glycol, propylene glycol dipelargonate and lauroglycol, alone or as a mixture, are preferentially employed, without this list being limiting.

A preferred emollient is propylene glycol.

Among the wetting agents, the role of which is to reduce the surface tension and to allow greater spreading of the liquid, compounds such as Pluronics type L44NF marketed by BASF and Synperonics type PE/L62 and PE/L44 marketed by Uniqema are preferentially employed, without this list being limiting.

Among the preservatives, exemplary thereof are benzoic acid and derivatives thereof with benzyl alcohol, benzalkonium chloride, sodium benzoate, bronopol, chlorhexidine, chlorocresol and derivatives thereof, ethyl alcohol, phenethyl alcohol, phenoxyethanol, potassium sorbate, diazolidinylurea, parabens such as propyl paraben or methyl paraben, either alone or as mixtures.

Preferred preservatives include parabens, phenoxyethanol or benzalkonium chloride, either alone or as a mixture.

The compositions according to the invention may comprise one or more emulsifiers.

Surfactant emulsifiers are amphiphilic compounds containing a hydrophobic portion with affinity for oil and a hydrophilic portion with affinity for water, thus creating a bond from the two phases. Ionic or nonionic emulsifiers thus stabilize oil/water emulsions by becoming adsorbed at the interface and by forming lamellar liquid crystal layers.

The emulsifying power of nonionic surfactants is closely linked to the polarity of the molecule. This polarity is defined by the HLB (hydrophilic/lipophilic balance).

A high HLB indicates that the hydrophilic fraction is predominant and, conversely, a low HLB indicates that the lipophilic portion is predominant. For example, HLB values of greater than about 10 correspond to hydrophilic surfactants.

Surfactants may be classified, according to their structure, under the generic terms "ionic" (anionic, cationic or amphoteric) or "nonionic". Nonionic surfactants are surfactants that do not dissociate into ions in water and are thus insensitive to pH variations.

Preferably, one or more high-HLB nonionic surfactant/low-HLB nonionic surfactant pairs will be used as emulsifying system: it may in particular be a nonionic emulsifying system comprising at least one nonionic surfactant with an HLB of greater than about 10 and at least one nonionic surfactant with an HLB of less than about 10.

The ratio of each of the two surfactants forming the above-mentioned pair is usually determined by calculating the required HLB of the fatty phase used.

Exemplary preferred emulsifiers include hydrophilic emulsifiers such as Tween 80, glyceryl stearate & PEG-100 stearate marketed under the trademark Arlacel 165FL® by Uniqema, copolyethers marketed under the trademark Synperonics such as PE/F68 by Uniqema; lipophilic emulsifiers such as Glucate SS and Glucamate SSE polyoxyethylene (21) stearyl ether marketed under the trademark Brij721® by Uniqema. Nonionic surfactants with a high HLB value that are also exemplary include sorbitan esters such as POE(20) sorbitan monooleate, marketed under the trademark "Tween 80" (HLB=15); POE(20) sorbitan monostearate marketed under the trademark "Tween 60" (HLB=14.9); fatty alcohol ethers such as POE(21) stearyl ether (HLB=15.5) or ceteareth 20 marketed under the trademark "Eumulgin B2" by Cognis (HLB=15.5), or low-HLB (lipophilic) nonionic surfactants, sorbitan esters, such as sorbitan monostearate (marketed under the trademark Span 60 by Uniqema), glycerol esters (marketed under the trademark Cutina GMSVPH by Cognis) such as glyceryl monostearate (Cutina GMS from Cognis), and low-HLB sucrose esters, for instance sucrose distearate.

The compositions according to the invention may also comprise a fatty phase. This fatty phase may comprise, for example, plant oils, mineral oils, animal oils, synthetic oils or silicone oils, and mixtures thereof.

Exemplary mineral oils include liquid paraffins of various viscosities such as Primol 352®, Marcol 82® and Marcol 152® marketed by Esso.

Plant oils that are exemplary include sweet almond oil, palm oil, soybean oil, sesame seed oil and sunflower oil.

Animal oils that are exemplary include lanolin, squalene, fish oil, mink oil with, as a derivative, squalane marketed under the trademark Cosbiol® by Laserson.

Synthetic oils that are exemplary include esters such as cetearyl isononanoate, for instance the product marketed under the trademark Cetiol SN® by Cognis France, diisopropyl adipate, for instance the product marketed under the trademark Ceraphyl 230® by ISF, isopropyl palmitate, for instance the product marketed under the trademark Crodamol IPP® by Croda, and caprylic/capric triglyceride such as Miglyol 812® marketed by Huls/Lambert Riviere.

Silicone oils that are exemplary include a dimethicone, for instance the product marketed under the trademark Dow Corning 200 Fluid®, a cyclomethicone, for instance the product marketed under the trademark Dow Corning 244 Fluid® by Dow Corning or the product marketed under the trademark Mirasil CM5® by SACI-CFPA.

Solid fatty substances such as natural or synthetic waxes may also be used. In this case, one skilled in the art will adapt the heating temperature of the preparation as a function of the presence or absence of these solids.

For the compositions according to the invention, liquid paraffins and more particularly Marcol 152® and Miglyol 812® are preferred.

The compositions of the invention may also comprise any additive usually employed in cosmetics or pharmaceuticals, such as surfactants, neutralizers, sunscreens, antioxidants, fillers, electrolytes, dyes, common mineral or organic acids or bases, fragrances, essential oils, cosmetic active agents, moisturizers, vitamins, essential fatty acids, sphingolipids, self-tanning compounds such as DHA, calmatives and skin-protecting agents such as allantoin, and pro-penetrating agents, or a mixture thereof. Needless to say, one skilled in the art will take care to select this or these optional additional compound(s), and/or the amount thereof, such that the advantageous properties of the compositions according to the invention are not, or are not substantially, adversely affected.

These additives may be present in the composition in a proportion of from 0.001% to 20% by weight relative to the total weight of the composition In one particular embodiment of the invention, the composition is in the form of an oil-in-water (O/W) emulsion of lotion, cream or cream-gel type and comprises:
from 0.1% to 0.3% of a naphthoic acid compound;
from 1% to 10% of at least one film-forming agent;
from 0.1% to 3% of gelling agents;
from 0.01% to 1.5% of chelating agents;
from 0.1% to 10% of a wetting agent;
from 0.1% to 20% of an emollient;
from 0.1% to 30% of fatty phase;
from 0.01% to 3% of preservatives;
from 0 to 10% of emulsifiers.

In one particularly preferred embodiment, the composition is in gel form and comprises:
from 0.1% to 0.3% of a naphthoic acid compound;
from 1% to 10% of at least one film-forming agent;
from 0.1% to 3% of gelling agents;
from 0.01% to 1.5% of chelating agents;
from 0.1% to 10% of a wetting agent;
from 0.01% to 3% of preservatives.

Optionally, the gel composition additionally comprises from 0.1% to 20% of an emollient.

The present invention also features administration of the compositions as described above, as medicaments, whether regime or regimen. The subject compositions are indeed useful as medicaments.

This invention also features a process for preparing the composition as described above. Such a process is characterized in that it comprises the step of mixing a physiologically acceptable vehicle which comprises at least one naphthoic acid compound with at least one film-forming agent, preferably selected from among compounds of polyvinylpyrrolidone type and derivatives or of polysaccharide type and derivatives or mixtures thereof, in order to obtain a composition in which the said naphthoic acid compound is in a form dispersed in the said composition.

The other possible excipients and additives will be introduced as a function of the chemical nature of the compounds and of the selected galenical form.

The preparation of a composition according to the invention is performed in 3 or 5 steps according to the selected galenical form, the 2 additional steps being performed solely for the preparation of forms of emulsion type such as creams, lotions or cream-gels.

Since the film-forming agent is of hydrophilic nature, it is introduced during the preparation of the hydrophilic phase when it is an emulsion. In the case of a gel, the film-forming agent is introduced into the aqueous phase after dispersion of the gelling agent(s) and before the neutralization step, as a function of the nature of the gelling agent(s).

Thus the process according to the invention comprises the following steps:

a) mixing the naphthoic acid compound with, optionally, at least one wetting agent and/or at least one chelating agent and/or at least one gelling agent and/or hydrophilic emulsifiers and/or one or more emollients (preferably at least one wetting agent and at least one chelating agent), in water, until the said naphthoic acid compound is fully dispersed, in order to provide the aqueous active phase;

b) mixing at least one film-forming agent with water in order to provide a film-forming phase;

c) introducing the film-forming phase obtained in b) into the aqueous active phase obtained in a) or vice versa in order to provide an aqueous composition.

As a function of the nature of the gelling agent, this agent may be introduced directly into the aqueous active phase or prepared in an independent gelling phase and added to the other phases constituting the composition according to the invention.

When the composition according to the invention is an emulsion comprising a fatty phase of the type such as creams, lotions or cream-gels, the process also includes, after step c), a step of mixing the aqueous composition obtained in c) with at least one fatty phase in order to obtain an emulsion.

The said fatty phase may be obtained by mixing at least one lipophilic emulsifier with at least one oil and/or one solid fatty substance.

The present invention also features application of the novel compositions as described above in cosmetics and dermatology.

In particular, the present invention relates to the application of the compositions as described above as pharmaceutical compositions for treating and/or preventing dermatological complaints, disorders or afflictions associated with a keratinization disorder that has a bearing on cell differentiation and proliferation, especially for treating common acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne and medication-related acne. In particular, the compositions according to the invention are useful in the treatment and/or prevention of dermatological complaints associated with a keratinization disorder that has a bearing on cell differentiation and proliferation, especially for treating common acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne and medication-related acne.

More particularly, this invention features administration of the compositions as described above as pharmaceutical compositions for preventing and/or treating simple acne.

The compositions according to the invention are preferentially administered topically. The term "topical route" means an administration to the skin, the integuments or the mucous membranes.

In addition, the present invention also features the cosmetic application of the subject compositions for the treatment of acne-prone skin, for combating the greasy appearance of the skin or the hair, in the protection against the harmful effects of sunlight or in the treatment of physiologically greasy skin, or for preventing and/or combating light-induced or chronological ageing.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Example of a Preparation Process for a Composition According to the Invention

Step a: Preparation of the Aqueous Active Phase:

Purified water, the active principle (adapalene), optionally the hydrophilic emulsifiers (such as Arlacel 165FL and Tween 80) in the case of producing an oil-in-water emulsion, the emollients (such as glycerol), the wetting agents (such as Synperonic PE/L62, Synperonic PE/L44), the chelating agent (such as EDTA) and optionally at this stage the gelling agent(s) (such as Carbopol, Pemulen TR1, Xantural, Methocel or Simulgel 600) are introduced with stirring using a deflocculator into a beaker that will serve as receiver for the finished product. The mixture is stirred without heating until fully dispersed. When the mixture is homogeneous, the aqueous phase is brought to 60° C. on a water bath and the preservative (such as methyl paraben) is introduced.

Step b: Preparation of the Film-Forming Phase:

The film-forming agent of polyvinylpyrrolidone type and derivatives or of polysaccharide type and derivatives or a mixture thereof is mixed with purified water.

Step c: Introduction of the Film-Forming Phase Obtained in b) into the Aqueous Active Phase Obtained in a) or Vice Versa:

Step d (optional): Preparation of the Fatty Phase:

The lypophilic emulsifiers (such as Glucate SS/Glucamate SSE 20 or Brij 721), the oily compounds (such as isostearic olepal, Cetiol SN, Crodamol DA, Speziol C18, Miglyol 812 or Cosbiol) and the preservatives (such as phenoxyethanol and propyl paraben) are introduced with stirring using a deflocculator into an additional beaker. The mixture is brought to 60° C. on a water bath and, after homogenization, the volatile silicone, if present, is introduced into the composition.

Step e (optional): Emulsification:

The fatty phase is introduced gently into the aqueous phase at a temperature of 60° C. and with stirring using a deflocculator, to perform the emulsification. Heating is maintained for 5 minutes and the hotplate is then removed to allow the product to cool gently. The stirring is regulated as a function of the viscosity. Steps d and e above are optional and are performed solely for the preparation of forms of the type such as emulsions such as creams, lotions or cream-gels.

Step f: Neutralization:

At 40° C., the gelling-agent neutralizer (such as triethanolamine or 10% sodium hydroxide solution) is introduced, if necessary, up to a pH of 5.5±0.5. The product then has a thicker consistency. At the end of manufacture, the pH is again checked. If it is within the norms, the sufficient quantity of water is added. The product is homogenized a final time in order to ensure good dispersion of the active principle adapalene (observation by microscope revealing a uniform dispersion free of aggregates) and the product is then packaged.

Formulations of Gel Type Containing 0.1% Adapalene with Kollidon VA64 (Copovidone) as Film-Forming Agent:

| Ingredients | Formula A | Formula B |
|---|---|---|
| Adapalene | 0.10% | 0.10% |
| Purified water | 79.50% | 79.50% |
| Carbopol 980 NF | 0.75% | 0.75% |
| Methyl paraben | 0.10% | 0.10% |
| EDTA | 0.10% | 0.10% |
| Propylene glycol | 4.00% | 4.00% |
| PEG 400 | 4.00% | 4.00% |
| Kollidon VA64 | 4.00% | 6.00% |
| Pluronic L44NF | 0.20% | 0.20% |
| Sodium hydroxide solution (10% m/m) | qs pH 5.5 ± 0.5 | qs pH 5.5 ± 0.5 |
| Purified water | qs 100% | qs 100% |

Process for Manufacturing Formulations A and B:
1) In a beaker, weigh out some of the purified water and the Carbopol 980 NF and mix together until fully dispersed at 800 rpm
2) Add the methyl paraben and the EDTA and mix together until fully dissolved at 800 rpm
3) In another beaker, weigh out the rest of the purified water and introduce the propylene glycol, the PEG 400 and the Kollidon VA64 with stirring at 800 rpm
4) After total dissolution, add the adapalene and the Pluronic L44NF and mix together at 500 rpm
5) Introduce the active phase into the first beaker and mix at 600 rpm
6) Neutralize with the sodium hydroxide solution to pH 5.5±05
7) Adjust to 100% with the purified water, if necessary Example 3

Formulations of Gel Type Containing 0.1% Adapalene with Sodium Hyaluronate as Film-Forming Agent

| Ingredients | Formula C |
|---|---|
| Adapalene | 0.10% |
| Purified water | 77.50% |
| Sodium hyaluronate | 2.00% |

-continued

| Ingredients | Formula C |
|---|---|
| Phenoxyethanol | 1.00% |
| EDTA | 0.20% |
| Propylene glycol | 4.00% |
| Synperonic PE/L62 | 0.20% |
| Purified water | qs 100% |

Process for Manufacturing Formulation C:
1) In a beaker, weigh out some of the purified water and the sodium hyaluronate and mix together at 800 rpm
2) In another beaker, weigh out the rest of the water, the EDTA, the propylene glycol, the Synperonic PE/L62 and the phenoxyethanol, and mix together until a clear solution is obtained, at 800 rpm
3) Introduce the adapalene and disperse using an Ultra-Turrax blender at 2400 rpm for 3 minutes
4) Introduce the active phase thus prepared into the first beaker and homogenize at 800 rpm
5) Adjust to 100% with the purified water, if necessary.

Example 4

Study of Stability of the Compositions According to the Invention a) Kollidon VA64 Gel:

| | | Formula A | | Formula B | |
|---|---|---|---|---|---|
| Time | Conditions | pH | Assay (%) | pH | Assay (%) |
| T zero | NA | 5.1 | 97.1 | 5.1 | 97.1 |
| 1 month | 5° C. | 5.1 | 102.3 | 5.1 | 96.2 |
| | 25° C./60 RH | 5.1 | 95.1 | 5.1 | 92.9 |
| | 40° C./75 RH | 5.1 | 96.7 | 4.9 | 97.7 |
| 2 months | 5° C. | 5.1 | 96.0 | 5.0 | 98.4 |
| | 25° C./60 RH | 5.1 | 97.0 | 5.1 | 101.9 |
| | 40° C./75 RH | 5.1 | 97.6 | 4.9 | 96.7 |
| 3 months | 5° C. | 5.0 | 95.5 | 4.9 | 97.0 |
| | 25° C./60 RH | 5.0 | 96.1 | 5.0 | 97.4 |
| | 40° C./75 RH | 4.9 | 97.7 | 4.7 | 97.7 | b) Sodium Hyaluronate Gel:

| Time | Conditions | Formula C Assay (%) |
|---|---|---|
| T zero | NA | 99.5 |
| 1 month | Room temperature | 97.9 |
| | 45° C./60 RH | |
| 3 months | Room temperature | 100.1 |
| | 40° C./75 RH | 100.2 |

Example 5

Tolerance Study of Gels with Film-Forming Agents Containing 0.1% Adapalene vs. 0.1% Differin Gel The present study is aimed at comparing the irritant power of a reference gel containing 0.1% adapalene with that of three 0.1% adapalene formulations in gel form containing a film-forming agent at various concentrations, and also placebos thereof, on the skin of the ear of the BALB/c mouse after repeated topical applications for 6 days.

The daily topical application (20 µl) of the test products is performed on the inner face of the ear of BALB/c mice divided into ten groups (female mice about 8 weeks old) at a rate of one application per day for 6 days.

The formulations tested are as follows:
Untreated
0.1% Differin Gel (DG)
Differin Gel placebo (DG plac.)
Kollidon VA64 gel placebo (AB plac.)
0.1% Kollidon VA64 (4%) gel (Formula A)
0.1% Kollidon VA64 (6%) gel (Formula B)
Hyaluronate gel placebo (C plac.)
0.1% Hyaluronate gel (Formula C)

| | ASC * D2-D19 | | % increase | |
|---|---|---|---|---|
| | Mean | Standard deviation | ASC vs. untreated | Student T-test vs. untreated |
| Untreated | 352.0 | 6.3 | — | — |
| Differin gel placebo | 352.0 | 1.1 | 0.0 | NS |
| 0.1% Differin gel | 519.8 | 43.1 | 47.7 | ** |
| Kollidon VA64 gel placebo | 359.8 | 3.9 | 2.2 | NS |
| Formula A: 0.1% Kollidon VA64 (4%) gel | 403.9 | 18.6 | 14.7 | * |
| Formula B: 0.1% Kollidon VA64 (6%) gel | 404.5 | 32.8 | 14.9 | NS |
| Hyaluronate gel placebo | 361.1 | 2.7 | 2.6 | NS |
| 0.1% Hyaluronate gel Formula C | 433.5 | 18.4 | 23.2 | ** |

* Area under the curve

The Kollidon VA64 and sodium hyaluronate placebo film-forming formulations are not irritant.

The Kollidon VA64 and sodium hyaluronate film-forming formulations are less irritant than the commercial reference Differin Gel.

0.1% Differin Gel increases the area under the curve by 48% relative to the untreated group.

The 0.1% Kollidon VA64 gels, irrespective of the content of Kollidon VA64 (4% or 6%), increase the area under the curve by 15% relative to the untreated group.

The 0.1% sodium hyaluronate gel increases the area under the curve by 23% relative to the untreated group.

The Kollidon VA64 and sodium hyaluronate film-forming formulations with 0.1% adapalene are less irritant than 0.1% Differin Gel.

Specifically, the comparison of the areas under the curve shows that:
the Kollidon VA64 4% to 6% gels, with 0.1% adapalene, decrease the area under the curve by 22% vs. 0.1% Differin Gel;
the sodium hyaluronate gel with 0.1% adapalene decreases the area under the curve by 16% vs. 0.1% Differin Gel.

Example 6

Study of In Vitro Release-Penetration of Kollidon VA64 (4%) Gel (Formula A) Containing 0.1% Adapalene vs. 0.1% Differin Gel (DG):

The present study compares in vitro the release-penetration into human skin without occlusion of adapalene formulated at 0.1% (m/m) in a gel containing 4% Kollidon VA 24 (Formula A) and a reference gel containing 0.1% adapalene.

The absorption studies were performed using excised human skin mounted under static conditions for a period of 16 hours. Three samples of skin were used. An amount of 10 mg of each formula (10 µg of adapalene) was applied to a 1 cm² area of skin. The adapalene concentrations in the fluid fractions collected over time and remaining in the skin at the end of the study were evaluated by the HPLC method with fluorescence detection (based on a validated method. Quantification limit: 1 ng·mL$^{-1}$).

|  | 0.1% Differin Gel | Formula A (Kollidon VA64 (4%) film-forming agent) |
|---|---|---|
| Concentration (% m/m) | 0.1 | 0.1 |
| Deposited dose (µg) | 7.03 ± 1.41 | 5.69 ± 0.45 |
| N | 6 | 6 |
| SC + epidermis |  |  |
| ng | 49.63 ± 35.72 | 60.94 ± 17.12 |
| % dose | 0.75 ± 0.59 | 1.08 ± 0.30 |
| Dermis |  |  |
| ng | 4.12 ± 5.12 | 1.37 ± 1.46 |
| % dose | 0.01 ± 0.01 | 0.03 ± 0.03 |
| Absorbed dose |  |  |
| ng | 0.62 ± 0.95 | LQL (lower than the quantification limit) |
| % dose | 0.01 ± 0.01 | LQL |
| Total amount penetrated |  |  |
| ng | 54.36 ± 32.10 | 62.31 ± 17.77 |
| % dose | 0.82 ± 0.54 | 1.10 ± 0.32 |
| Mass balance |  |  |
| µg | 6.05 ± 1.15 | 4.95 ± 0.56 |
| % dose | 86.21 ± 3.14 | 86.87 ± 4.62 |

Conclusions of the Study:

The 0.1% Differin Gel and Kollidon VA64 Gel formulations have the same SC+epidermis/dermis distribution profile with the majority of the adapalene present in the upper layers of the skin.

The total amount of adapalene penetrated is slightly higher with the Kollidon VA64 Gel formulation.

General Conclusion:

The gel formulation containing Kollidon VA64 improves the tolerance of adapalene without modifying the distribution profile or the total amount penetrated.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, dermatological/cosmetic gel composition useful for the treatment of acne, comprising at least one naphthoic acid compound essentially uniformly distributed therethrough, said at least one naphthoic acid compound having the formula (I):

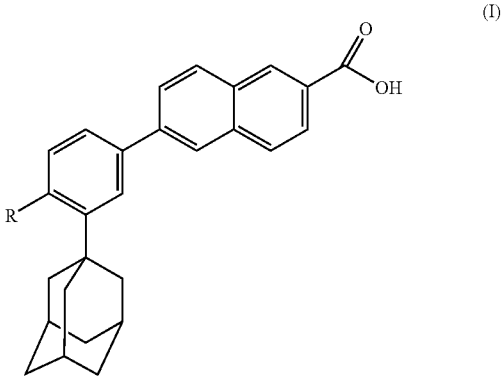

in which R is a hydrogen atom, a hydroxyl radical, a branched or unbranched alkyl radical having from 1 to 4 carbon atoms, an alkoxy radical having from 1 to 10 carbon atoms or a cycloaliphatic radical, and an amount of at least one hydrophilic film-forming agent formulated into a topically applicable, physiologically acceptable medium therefor as an aqueous gel, said aqueous gel having a pH of 5.5±0.5, wherein said at least one film-forming agent comprises copovidone.

2. The dermatological/cosmetic gel composition as defined by claim 1, wherein the concentration of the at least one naphthoic acid compound ranges from 0.001% to 10%, by weight relative to the total weight thereof.

3. The dermatological/cosmetic gel composition as defined by claim 1, said at least one naphthoic acid compound being selected from the group consisting of 6-[3-(1-adamantyl)-4-methoxyphenyl]-2-naphthoic acid, 6-[3-(1-adamantyl)-4-hydroxyphenyl]-2-naphthoic acid, 6-[3-(1-adamantyl)-4-decyloxyphenyl]-2-naphthoic acid and 6-[3-(1-adamantyl)-4-hexyloxyphenyl]-2-naphthoic acid.

4. The dermatological/cosmetic gel composition as defined by claim 3, said at least one naphthoic acid compound comprising 6-[3-(1-adamantyl)-4-methoxyphenyl]-2-naphthoic acid.

5. The dermatological/cosmetic gel composition as defined by claim 4, wherein the concentration of said 6-[3-(1-adamantyl)-4-methoxyphenyl]-2-naphthoic acid is about 0.1% by weight relative to the total weight thereof.

6. The dermatological/cosmetic gel composition as defined by claim 4, wherein the concentration of said 6-[3-(1-adamantyl)-4-methoxyphenyl]-2-naphthoic acid is about 0.3% by weight relative to the total weight thereof.

7. The dermatological/cosmetic gel composition as defined by claim 1, wherein the concentration of said at least one film-forming agent ranges from 0.5% to 20% by weight relative to the total weight thereof.

8. The dermatological/cosmetic gel composition as defined by claim 7, wherein the concentration of said at least one film-forming agent is 2%, 4% or 6% by weight relative to the total weight thereof.

9. The dermatological/cosmetic gel composition as defined by claim 1, which comprises, in water:
   from 0.1% to 0.3% of at least one naphthoic acid compound;
   from 1% to 10% of at least one film-forming agent;
   from 0.1% to 3% of gelling agents;
   from 0.01% to 1.5% of chelating agents;
   from 0.1% to 10% of a wetting agent; and
   from 0.01% to 3% of preservatives.

10. The dermatological/cosmetic gel composition as defined by claim 1, which comprises, in water:
- from 0.1% to 0.3% of at least one naphthoic acid compound;
- from 1% to 10% of at least one film-forming agent;
- from 0.1% to 3% of gelling agents;
- from 0.01% to 1.5% of chelating agents;
- from 0.1% to 10% of a wetting agent; and
- from 0.1% to 20% of an emollient;
- from 0.01% to 3% of preservatives.

11. A process for preparing a dermatological/cosmetic gel composition as defined by claim 1, comprising mixing a physiologically acceptable vehicle which comprises said at least one naphthoic acid compound with said at least one film-forming agent, and neutralizing, if necessary, to provide a gel composition in which said at least one naphthoic acid compound is in a form dispersed therein.

12. The process as defined by claim 11, which comprises the following steps:
   a) mixing said at least one naphthoic acid compound with at least one wetting agent, and at least one chelating agent in water, until said at least one naphthoic acid compound is fully dispersed, to provide an aqueous active phase;
   b) mixing said at least one film-forming agent with water to provide a film-forming phase;
   c) introducing said at least one film-forming agent obtained in b) into the aqueous active phase obtained in a), or vice versa, and neutralizing, if necessary.

13. A method for the treatment of acne, comprising topically applying onto the affected skin area of an individual in need of such treatment, a thus effective amount of the dermatological/cosmetic gel composition as defined by claim 1.

14. A method for treating common acne, comedonal acne, papulopustular acne, papulocomedonal acne, nodulocystic acne, acne conglobata, acne keloid of the nape of the neck, recurrent military acne, acne necrotica, acne neonatorum, occupational acne, acne rosacea, senile acne, solar acne or acne medicamentosa, comprising topically applying onto the affected skin area of an individual in need of such treatment, a thus effective amount of the dermatological/cosmetic gel composition as defined by claim 1.

15. A method for the treatment of common acne, comprising topically applying onto the affected skin area of an individual in need of such treatment, a thus effective amount of the dermatological/cosmetic gel composition as defined by claim 1.

* * * * *